United States Patent [19]
McGuinness

[11] Patent Number: 6,156,062
[45] Date of Patent: Dec. 5, 2000

[54] HELICALLY WRAPPED INTERLOCKING STENT

[75] Inventor: Colm P. McGuinness, Renmore, Ireland

[73] Assignee: Ave Connaught, Dublin, Ireland

[21] Appl. No.: 08/984,404

[22] Filed: Dec. 3, 1997

[51] Int. Cl.[7] ..................................................... A61F 2/06
[52] U.S. Cl. ............................. 623/1.11; 623/12; 606/198
[58] Field of Search ................................. 623/1, 12, 1.11, 623/1.38, 902; 606/198

[56] References Cited

U.S. PATENT DOCUMENTS

| 4,762,128 | 8/1988 | Rosenbluth . | |
|---|---|---|---|
| 5,147,370 | 9/1992 | McNamara et al. . | |
| 5,163,952 | 11/1992 | Froix | 623/12 |
| 5,441,515 | 8/1995 | Khosravi et al. | 623/1 |
| 5,443,477 | 8/1995 | Marin et al. . | |
| 5,476,505 | 12/1995 | Limon | 606/198 |
| 5,500,013 | 3/1996 | Buscemi et al. | 623/1 |
| 5,507,767 | 4/1996 | Maeda et al. | 623/1 |
| 5,591,196 | 1/1997 | Marin et al. . | |
| 5,618,300 | 4/1997 | Marin et al. . | |
| 5,670,161 | 9/1997 | Healy et al. . | |
| 5,824,053 | 10/1998 | Khosravi et al. | 606/195 |

FOREIGN PATENT DOCUMENTS

WO 83/00997  3/1983  WIPO .
WO 93/07412  4/1993  WIPO .

Primary Examiner—Paul B. Prebilic
Attorney, Agent, or Firm—Sterne, Kessler, Goldstein & Fox P.L.L.C.

[57] ABSTRACT

The present invention concerns an expandable stent for supporting a body lumen formed from an elongate strip of biocompatible material that is helically wrapped into a tubular shape. The strip is formed with a tongue extending along one edge and a groove along the other. The tongue is slidably received in the groove as the strip is wound into helical wraps that form a tube. The tongue and groove engagement interlocks the wraps to maintain the tubular shape. Sliding of the tongue within the groove permits the wraps to slide relative to each other causing the diameter of the stent to be increased or decreased. An increase in the stent diameter corresponds to a decrease in the length of the stent and vice versa. Thus the stent can be delivered to a vessel site in reduced diameter long length configuration, then deployed by compressing its length to cause expansion. Preferably, the stent is formed from a polymeric and bioabsorbable material that can be loaded with a pharmaceutical to provide localized drug delivery.

19 Claims, 6 Drawing Sheets

HELICALLY WRAPPED INTERLOCKING STENT

FIELD OF THE INVENTION

This invention relates to stents implantable within the body of a patient to support a body lumen.

BACKGROUND OF THE INVENTION

Stents have gained acceptance in the medical community as a device capable of supporting body lumens, such as blood vessels, that may have become weakened or susceptible to closure. Typically, a stent is inserted into a vessel of a patient after an angioplasty procedure has been performed to open a stenosed region of a vessel. After the catheter used to perform angioplasty has been removed from the patient, a tubular stent maintained in a small diameter delivery configuration at the distal end of a delivery catheter can be navigated through the vessels to the site of the stenosed area. Once positioned at the site of the stenosis, the stent is released from the delivery catheter and expanded radially to contact the inside surface of the vessel. The expanded stent provides a scaffold-like support structure to maintain the patency of the region of the vessel engaged by the stent, thereby promoting blood flow.

Currently, a variety of stent designs exist having differing mechanisms of expansion, materials, surface configurations and methods of manufacture. Some expandable stents are expanded from a compact delivery diameter to a larger, implanted diameter by the inflation of a balloon located within the stent. Alternatively, stents may be expanded by internal forces in the stent material such as resilient forces created by elastic deformation of the stent to its smaller diameter or by the forces created within a shape memory alloy material, such as nitinol, upon temperature elevation. Various biocompatible materials can be used for a stent such as stainless steel, nitinol and a wide range of polymers, including bioabsorbable materials. Methods of making a stent include coiling or bending wire into a tubular shape, perforating a flat sheet of material and rolling it into a tube or perforating a preformed tube so that it becomes expandable. Many of these known stents require multiple steps to manufacture and require the use of materials that are difficult to form, increasing costs. It would be desirable to provide a stent that is simple and economical to manufacture, performs reliably and is simple to use. The present invention addresses those objectives.

SUMMARY OF THE INVENTION

The stent of the present invention is formed from an elongate strip of biocompatible material that is helically configured to form a tubular structure. The strip has two opposing edges parallel to a major longitudinal axis that are formed to have a groove and a tongue receivable within the groove to provide interlocking capability of the edges. Although the tongue and groove engagement locks the edges together, sliding movement between the edges is possible so that wraps formed by the helically arranged strip can be slid relative to each other, effectively decreasing or increasing the diameter of the tube. The line of engagement of the tongue and groove extends helically around the resulting tube as a helical rib.

As the edges of the strip slide relative to each other, the length and diameter of the stent change interdependently. Therefore, an increase in diameter of the stent corresponds to a reduction in length as the edges of the helical wrapping twist and slide relative to one another and the pitch of the helical rib formed by their engagement decreases. Likewise, decreasing the diameter of the stent causes a corresponding increase in length as the pitch of the helical rib increases.

The interdependency of length and diameter of the present stent facilitates its delivery into a body lumen such as a blood vessel. Delivery of the stent into a vessel can be accomplished by elongating the stent to obtain a smaller delivery diameter, then shortening the stent to increase the diameter for deployment within the vessel. Contact between the surfaces of the tongue and groove is such that sliding movement is possible to change the diameter of the stent when intended, yet frictional contact prevents unwanted diameter change of the stent after implantation. The force required to overcome the frictional engagement of the tongue and groove is sufficiently high to withstand the compressive force placed on the stent by the vessel that is being maintained in an open configuration. Therefore, the stent will not collapse after it has been deployed in the vessel. Additionally, the tongue and groove surfaces may be provided with ratcheting teeth so that sliding movement between them can occur in only one direction, the expansion direction. A ratcheting tongue and groove connection provides an additional mechanism for locking the stent in an expanded configuration despite the radially compressive force of the vessel.

Deployment of the stent within the vessel may be accomplished through a catheter, such as a guide catheter, that has been navigated to the deployment site. While the stent is in a small diameter delivery configuration, it is pushed through the catheter by a pusher shaft and ejected from the distal end of the catheter at the deployment site.

The stent is expanded to contact with the vessel wall by shortening its length. An elongate member such as a flexible shaft or string can be attached to the distal end of the stent and extended proximally back through the stent and catheter for manipulation outside the patient. Pulling on the string in a proximal direction while the proximal end of the stent butts up against the distal end of the pusher shaft places a compressive force on the stent sufficient to cause sliding between the tongue and groove of the helically wrapped strip that forms the stent. As the stent shortens, its diameter expands.

Alternatively, the stent may be delivered through a guide catheter and expanded by a coaxial shaft that is releasably joined to the interior of the stent at both ends. By rotating the coaxial shafts relative to each other to rotate the ends of the stent, the wraps of the stent are slid relative to each other to expand the stent. This method of delivery also provides stent retraction capability while the coaxial pusher shaft remains attached to the stent interior. If the stent is expanded in the wrong position, the ends of the stent can be rotated in relative directions to elongate the stent and reduce its diameter so that it can be repositioned within the vessel.

Additionally, after deployment of the stent by either of the above delivery methods, it may be further expanded into the vessel wall by the radially expansive force of a balloon of a balloon catheter positioned within the stent. The stent's initial delivery and expansion can also be performed with a balloon angioplasty catheter. With this delivery method, the stent's diameter is reduced into contact with the balloon of the balloon catheter and the combination delivered through the guide catheter to the vessel location. Inflation of the balloon within the stent at the vessel deployment site causes the wraps of the stent to slide relative to each other to expand the diameter of the stent.

The tongue and groove can be formed to project slightly from the surface of the strip to create a helical projecting rib around the exterior of the stent that anchors into the vessel wall during deployment to help locate the stent. Alternatively, the tongue and groove can be formed into the edge of the strip, so as not to project from the stent surface, thereby creating a smooth exterior surface on the formed stent. Though the anchoring rib is absent from this version of the stent, the profile of the stent is minimized to facilitate delivery into narrow vessels.

The stent is preferably made from a polymer material so that it may be economically manufactured as a unitary plastic strip by extrusion or injection molding. However, the stent may also be formed from biocompatible metals such as nitinol or stainless steel by processes such as micro-machining. In the case of polymers, the material of the stent may be bioabsorbable, permitting the stent to dissolve after time within the patient's body. Additionally, the polymer stent may be impregnated with a pharmaceutical such as an anticoagulant or other medicine suited to aid recovery of the affected vessel.

It is an object of the present invention to provide a stent that is reliable yet simple and cost effective to manufacture.

It is another object of the invention to provide a stent that can be reliably and safely expanded from a reduced delivery diameter to a larger deployed diameter.

It is yet another object of the invention to provide a stent that can be easily fabricated from polymer materials and made to be bioabsorbable or capable of carrying pharmaceutical agents for localized drug delivery within the vessel.

It is yet another object of the invention to provide a stent that is free from sharp edges that could rupture a dilatation balloon upon contact with a stent.

It is yet another object of the invention to provide a stent formed from a single component.

It is another object of the invention to provide a stent that is capable of having a wide variety of surface configurations.

It is another object of the invention to provide a stent that can be retracted for repositioning after it has been expanded in the vessel.

DETAILED DESCRIPTION OF THE DRAWINGS

The foregoing and other objects and advantages of the invention will be appreciated more fully from the following further description thereof with reference to the accompanying drawings wherein:

FIG. 5B is a diagrammatic side view of a pusher shaft used to deliver the stent;

DESCRIPTION OF THE ILLUSTRATIVE EMBODIMENTS

Figures 1, 2, 2A, 3:
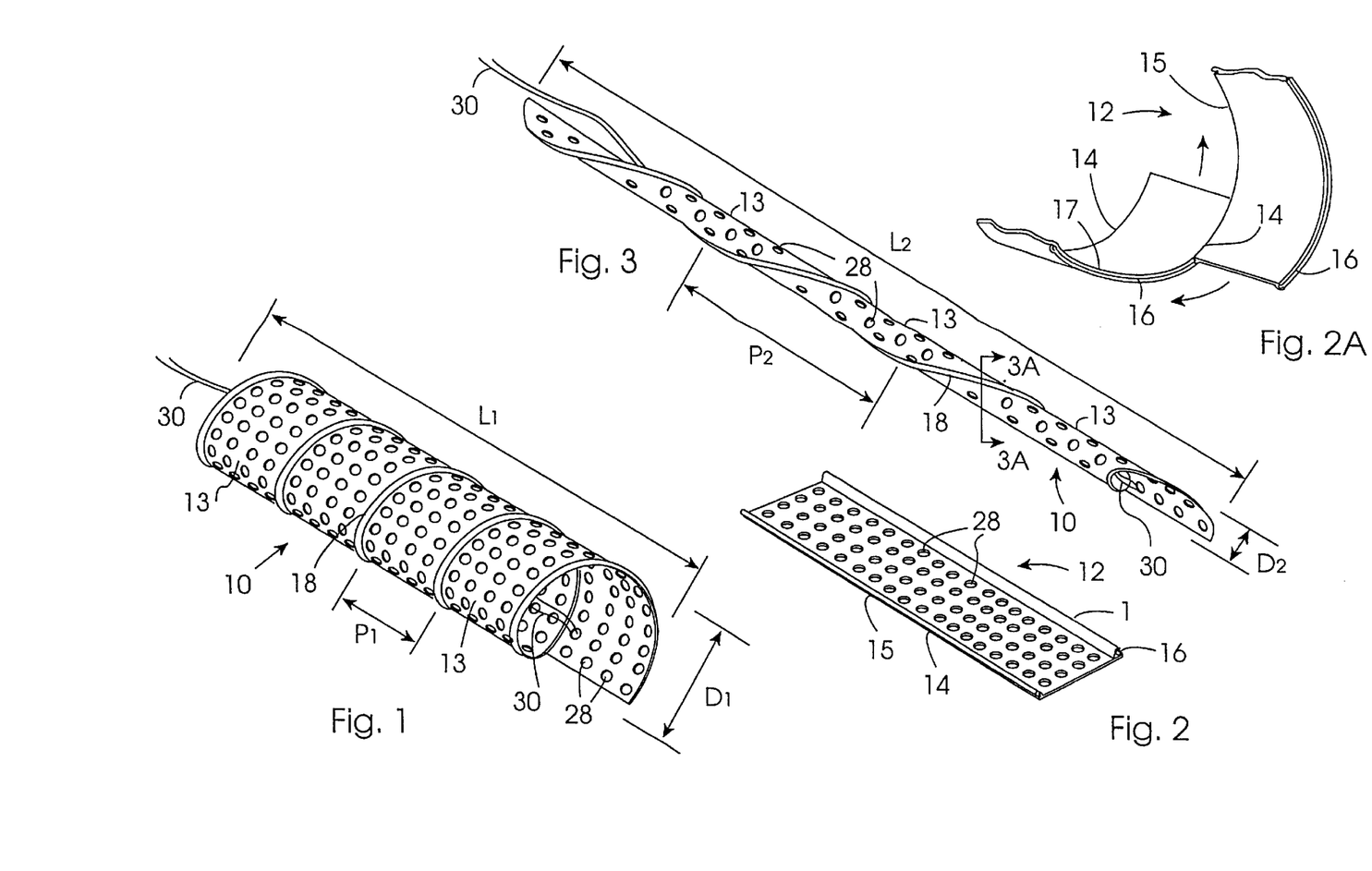
FIG. 1 is an isometric view of an embodiment of the stent of the present invention.
FIG. 2 is an isometric view of a segment of a strip of material prior to wrapping in a helical form to create the stent.
FIG. 2A is a fragmented isometric view of the ends of the strip being joined together.
FIG. 3 is an isometric view of the stent of the present invention in a reduced delivery diameter and elongated length.

FIG. 1 shows an embodiment of the helically wrapped interlocking stent 10 in an expanded configuration. The stent is formed from a flat, thin strip 12 of material, such as that shown in FIG. 2, that is helically wrapped into a tubular shape. The strip has a tongue 14 formed along one edge 15 and a corresponding groove 16 formed along the opposite edge 17. The tubular stent 10 is formed by bringing together opposite corners of the strip 12 and engaging tongue 14 into groove 16 as shown in FIG. 2A, to begin a helically wrapped tube that will become the stent. The strip is configured so that the tongue becomes interlocked within the groove yet relative sliding movement between them is permitted. Thus, as the edges of the strip are slid relative to each other in opposite helical directions, the strip becomes configured into a series of planar coils or wraps 13, creating a tube that forms the stent 10.

Continuing to slide the edges 15 and 17 of the strip relative to each other creates several wraps 13 and forms a tube as shown in FIG. 1. The joint of the tongue and groove forms a helically extending rib 18 around the stent that defines the wraps 13. As the wraps 13 of the strip 12 are slid relative to each other, the length and diameter of the tube and pitch of the rib 18 all vary interdependently. Thus, when the wraps 13 forming the tube shown in FIG. 1 are slid relative to each other, to extend the length from L1 to a length of L2 as shown in FIG. 3, the diameter reduces from D1 to D2 and pitch (distance between helical windings of the rib along a longitudinal line on the surface of the stent) increases from P1 to P2. Conversely, sliding the wraps 13 in opposite relative directions causes a reduction in length from L2 to L1, increase in diameter from D2 to D1 and decrease in pitch from P2 to P1 to achieve the expanded stent size shown in FIG. 1. The interrelationship of diameter and length makes the present invention well suited for use as an expandable stent, as it can be easily inserted into a vessel in a reduced diameter configuration having a longer length that can then be shortened to cause the stent to expand to support the vessel at the intended location.

Figure 3A:
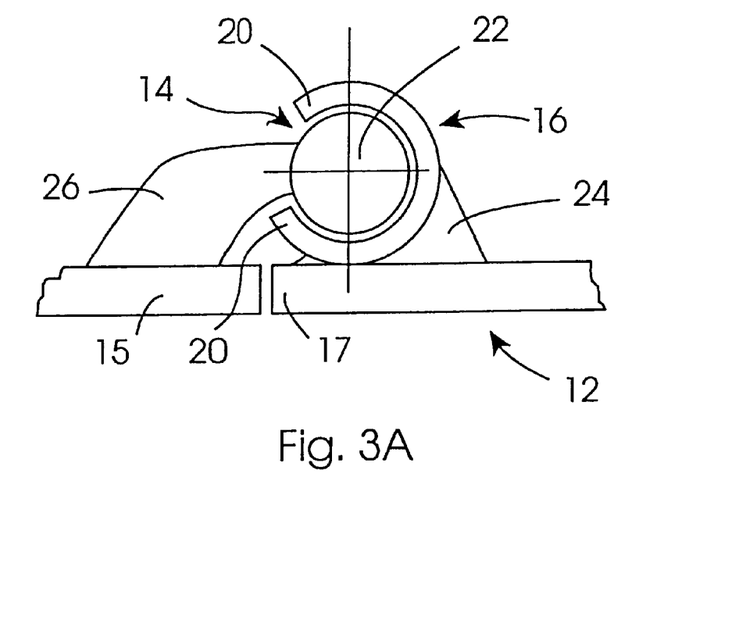
FIG. 3A is a cross-sectional view of the tongue and groove engagement configuration as seen at the line 3A—3A of FIG. 3.

FIG. 3A shows an example of a tongue and groove configuration, employed on the edges 15 and 17 of the strip 12 shown in FIGS. 1–3, that is suitable to provide an interlocking engagement that permits sliding movement between the tongue 14 and groove 16. In the example of 3A, the groove 16 has a C-shaped cross-sectional shape to receive a tongue 14 having a circular cross-sectional shape. The ends 20 of the C-shaped groove 16 are supported on the surface of the strip 12 along the edge 17 by a groove extension 24. A tongue extension 26, likewise serves to support and hold the tongue along the entire edge 15 in a cantilever fashion. The extensions 24 and 26 elevate the tongue and groove engagement over the stent surface to permit the edges 15 and 17 meet directly to form a continuous stent surface. The groove extension 24 and tongue extension 26 are each integrally formed with the corresponding tongue and groove and with the strip 12.

The groove ends 20 surround a sufficient amount of surface area of the circular cross-section tip 22 of the tongue 14 so that the tongue is restrained from lateral movement out of the groove. However, a slight clearance between the surfaces of the circular shaped tongue 14 and C-shaped groove 16 permits some sliding between them in a longitudinal direction to enable expansion of the stent. The clearance also permits slight misalignment of the tongue within the groove upon radially compressive loading of an expanded stent by the vessel. The loading force vectors accompanying the misalignment tend to lock the tongue within the groove to resist sliding movement between them and the resulting contraction of the stent under the compressive forces exerted by the vessel. Examples of suitable dimensions and clearances for proper tongue and groove engagement are as follows: groove 16 diameter equals 0.11 mm, tongue tip 22 diameter equals 0.09 mm, tongue extension 26 thickness equals 0.04 mm and opening between the ends 40 of the C-shaped groove receiving tongue extension equals 0.06 mm. The above listed dimensions are intended to be illustrative and it is recognized that other dimensions can be used to produce a functional device in accordance with the invention.

Raising the helical rib 18 from the surface of the stent 10 by employing the extensions 24 and 26 as described above provides an anchor to help maintain the stent in position within the vessel. A rib that projects slightly from the outside surface of the stent may be pressed into the wall of the vessel during stent expansion and become embedded, serving to anchor the stent. The amount of the rib's extension from the surface of the stent can be varied by changing the length of extensions 24 and 26 and by changing the size of the tongue and groove to increase or decrease the prominence of the rib on the surface of the stent.

Figure 3B:
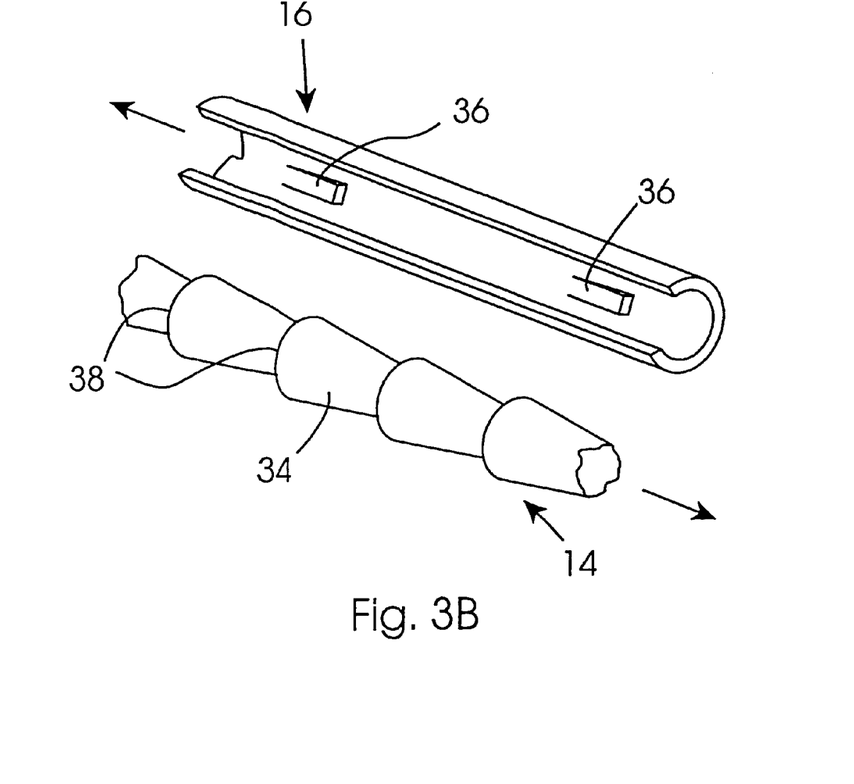
FIG. 3B is an isometric view of a fragment of the tongue and corresponding groove employing a ratcheting mechanism.

Additionally, the tongue and groove surfaces may be formed with a ratcheting mechanism to help resist relative sliding movement between them in the direction of stent radial contraction. The ratcheting mechanism helps to maintain the stent in its expanded configuration in the face of the radially compressive force being applied around the stent by a weakened vessel being supported. As shown in FIG. 3B, the ratcheting mechanism may comprise angled teeth 34 formed on the surface of either the tongue 14 or the groove 16 and at least one flexible pawl 36 arranged on the other surface to engage the teeth. The teeth and pawl may be formed simultaneously with the formation of the strip during injection molding or may be formed by stamping or machining after the strip is formed by a process such as extrusion. In this particular ratcheting arrangement, the pawls 36 formed in the groove flex to permit the angled teeth of the captured tongue to slip as the tongue and groove are slid relative to each other in directions shown by the arrows. However, when the tongue 14 is moved in the opposite direction relative to the groove 16, the back edges 38 of the teeth 34 catch onto the pawls 36 preventing relative sliding movement of the tongue and groove.

Figure 4:
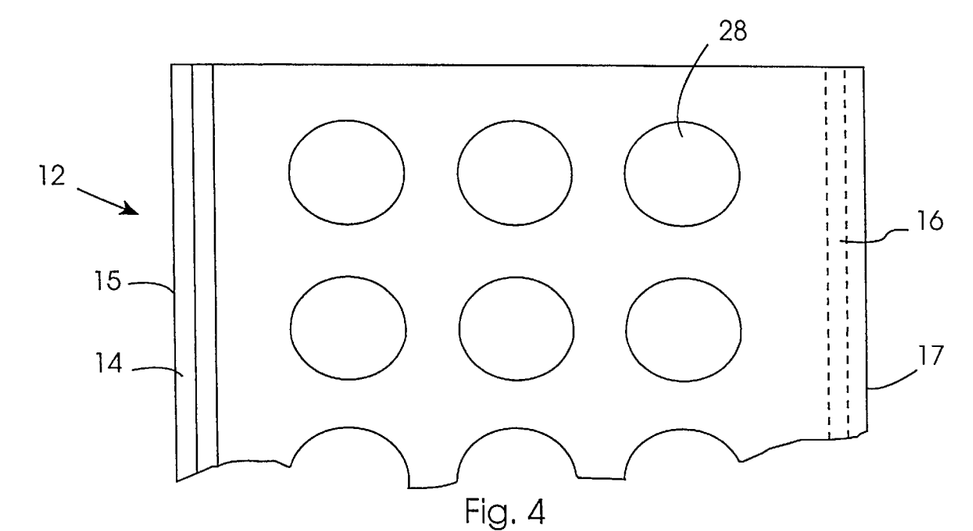
FIG. 4 is a top view of a segment of a strip of material to be used for forming a stent according to a second embodiment of the invention.
Figure 4A:
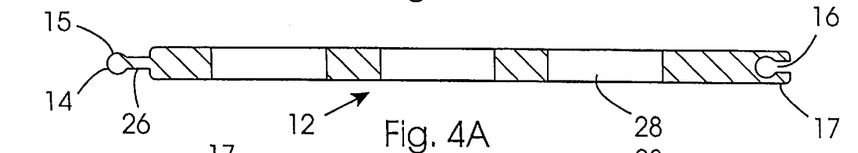
FIG. 4A is a side view of a strip of material to be used to form a stent according to a second embodiment of the invention.
Figure 4B:
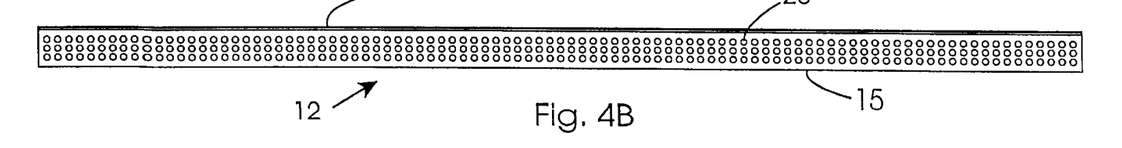
FIG. 4B is a top view of a strip of material to be used to form a stent according to a second embodiment of the present invention.

FIGS. 4–4B show a second embodiment of the strip 12 used to form a stent having a smooth outer surface, without a projecting rib. The groove is formed within the edge 17 of the strip and the tongue projects from the opposite longitudinal edge 15 of the strip so that when the tongue and groove are interlocked, a smooth transition exists between the edges. However, aside form the absence of a projecting helical rib, the tongue and groove engagement of the second strip embodiment operates identical to that of the first strip embodiment described above. Without the rib, the stent formed from the second strip embodiment has a lower profile than the stent with the rib. Thus the lower profile stent can be delivered through a smaller diameter catheter capable of reaching smaller diameter vessels than could be serviced by the ribbed stent of the first embodiment. Though the second embodiment of the stent provides the advantage of a lower profile, the size of the tongue and corresponding groove is dependent upon the thickness of the strip into which they are formed. The tongue and groove of the stent of the first embodiment are not dependent on strip thickness because they are formed above the strip edge rather than within it. Therefore if design considerations require a thicker tongue and groove connector system, the stent of the first embodiment may be preferred.

The strip 12 used to form the stent 10 is preferably formed of a polymeric material, although other flexible, durable and easily formable materials may be suitable. A polymeric strip having an integrally formed tongue and groove can be easily formed by injection molding or extrusion. Alternatively, a strip of biocompatible metal such as nitinol or stainless steel could be formed by micro-machining or laser cutting. Regardless of material chosen, the tongue 14 and groove 16 configurations are preferably integrally formed at the edges of the strip of material during strip formation to create a unitary member. The strip 12 should be flexible and thin to occupy as little space within the vessel as possible. A strip thickness on the order of 0.2 mm has been found to be functional. The tongue and groove of dimensions described above can be employed within the edges of a strip 12 having a thickness of 0.2 mm. Suitable dimensions for the strip prior to being rolled into a stent have been found to be on the order of 75 mm in length by 3 mm in width. However, other dimensions could be suitable for the strip depending on the desired size of the resulting stent.

Additionally, the strip 12 of either embodiment may have formed throughout its surface a series of openings 28 to permit blood to reach the vessel lined by the stent. The openings 28 may be of any desired size, shape and quantity, but a sufficient amount of material should remain to preserve the structural integrity of the strip. The openings may be formed during the formation of the strip, such as during injection molding, or may be created after the strip has been formed as would be the case for an extruded strip. Alternatively, the strip can be formed without openings to create a stent with a solid, continuous surface. However, though a solid wall is believed to optimize smooth blood flow through the stent, it may be desirable to permit some blood to contact the vessel wall to aid in healing of the affected vessel area. Therefore, the number and orientation of openings formed into the stent can be custom tailored to obtain the best compromise between smooth flow and vessel wall contact with the blood.

In the case of a polymer stent, it may be desirable to select a bioabsorbable polymer material so that the stent does not remain permanently implanted within the patient. The stent of the present invention can be made from a bioabsorbable material such as Poly(L-lactide) (PLLA) or a Polyglycolic acid, both of which are available from Boehringer Ingelheim KG, Chemicals Division, D-55216 Ingelheim, Germany. A stent made from a bioabsorbable material dissolves in the patient after serving its function to support the vessel. The bioabsorbable material can be made to degrade as quickly as approximately three months. However, it is expected that in most applications for the present stent, a service life of approximately nine months to one year will be desirable. Exact parameters for injection molding or extruding the strip from the bioabsorbable material depend on the molecular weight of the material selected.

In addition to making the stent bioabsorbable, it may be desirable for some applications to impregnate the polymer material of the stent with a pharmaceutical agent useful in treating the affected area of the vessel. Impregnating the stent material during its manufacture with a drug permits localized drug delivery that is believed to be more effective and safer than administering the drugs through the blood stream generally. Typically, anticoagulants are administered to patients after receiving a stent to prevent thrombosis from developing around the foreign object newly implanted in the blood stream. As general administration of an anticoagulant renders a patient vulnerable to uncontrolled bleeding resulting from even a small cut or injury, the patient must remain hospitalized until the drug has dissipated from the body. Localized delivery of the anticoagulant by stent impregnation eliminates the danger to the patient of uncontrolled bleeding and the required hospital stay. Therefore, implantation of a drug loaded stent may be accomplished in a one-day outpatient procedure, greatly reducing cost and inconvenience to the patient.

The interdependently variable diameter and length of the stent provides several simple and effective delivery options involving introducing the stent through the vasculature in a compact delivery diameter and then expanding it at the intended vessel location. The stent of the present invention can be reduced to a compact delivery diameter on the order of 1.5 mm and can be expanded to a size on the order of 3.5 mm. In a preferred method of delivery shown in FIG. 5, a guidewire (not shown) and guide catheter 40 are first navigated through the vessel 42 to the deployment site in a conventional manner. A conventional guidewire and 6F guide catheter can be used, though the guide catheter size can be varied to suit the vessel size to be treated. After reaching the intended location, the guidewire is removed and the stent 10, in a reduced diameter and extended length configuration, is introduced into the proximal end of the guide catheter lumen 41. A pusher shaft 44 is then inserted into the proximal end of the guide catheter 40, behind the stent, and advanced distally to push the stent through the guide catheter lumen 41 and out the distal end to the vessel deployment site. Radiopaque markers can be joined to the pusher shaft 44 or stent 10 to enhance fluoroscopic visibility and thus facilitate positioning of the stent within the vessel.

Figure 5:
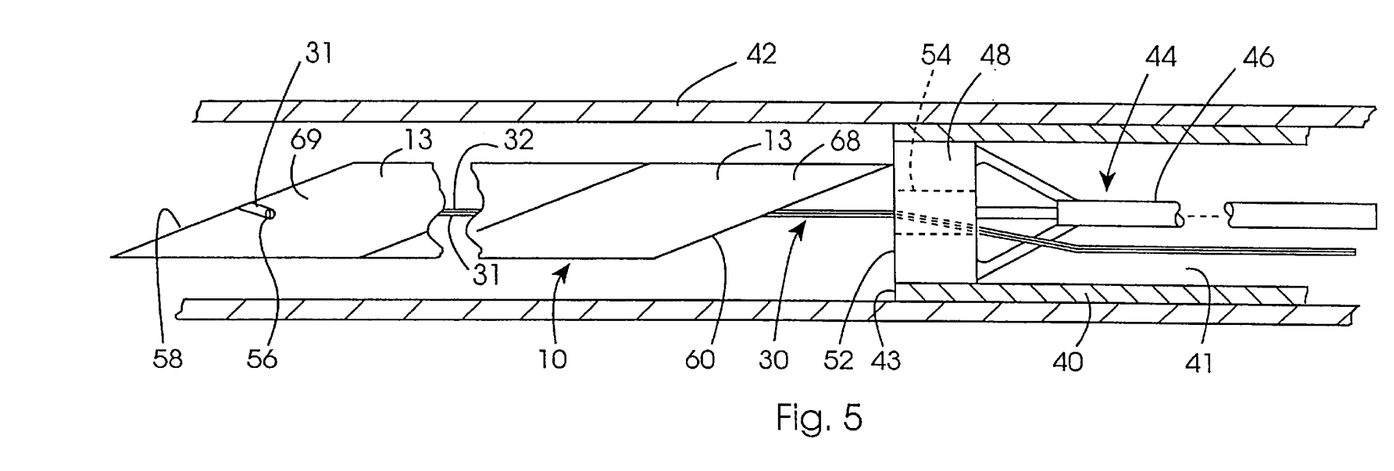
FIG. 5 is a diagrammatic cut away view of the stent being delivered in a vessel by a delivery system embodiment.
Figure 5A:
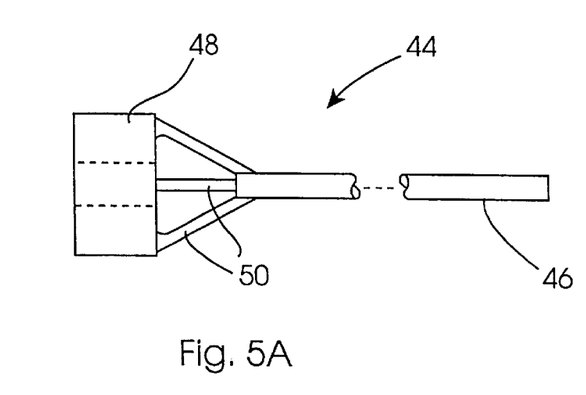
FIG. 5A is a diagrammatic front view of a pusher shaft used to deliver the stent.

The pusher shaft 44, shown in FIGS. 5, 5A and 5B comprises an elongate flexible shaft 46 having a pusher 48 at its distal end. The shaft may be solid or hollow and may be made from any flexible biocompatible material such as a stainless steel or a polymer or nitinol. The shaft should be fabricated to have sufficient column strength to push the stent through the guide catheter. The pusher is of a greater diameter than the shaft 46 and is sized to occupy most of the cross-sectional area of the guide catheter lumen 41 to push the stent effectively while remaining slidable within the lumen 41. A suitable pusher diameter for use with a 6F guide catheter is approximately 1.6 mm. The distal face 52 of the pusher is substantially solid, to provide a contact surface for the stent, but also employs a small central through-hole 54 on the order of 0.5 mm in diameter to permit a stent pull string 30 to pass through proximally. The pusher 48 can be joined to the smaller diameter shaft 46 by angularly extending arms 50. The arms and pusher can be bonded or molded to the shaft 46 or the shaft and pusher can be integrally molded as one piece from a polymer material.

As shown in FIG. 5, an elongate flexible pulling member such as a pull string 30 is joined to the distal end of the wrapped stent 10, to provide a mechanism for shortening the length, and thereby expanding the diameter, of the stent from outside the patient. Other variations of the pulling member are possible such as a wire or any elongate flexible shaft sized small enough to fit within the guide catheter and stent and having sufficient tensile strength to pull and compress the stent. The pull string can be joined to the distal end of the stent by looping a first lead 31 through a hole 56 or opening 28 in the sidewall of the stent. The first lead 31 of the string 30 returns into the stent either through another adjacent hole or opening or through the stent distal opening 58. The first lead 31 extends through the stent parallel to a second lead 32 of the string 30 and out the stent proximal opening 60. During delivery of the stent, the leads of the string extend proximally from the stent, through the hole 54 of the pusher and the lumen 41 of the guide catheter 40 and out of the patient where it can be manipulated for expanding the stent. After the stent is pushed out of the distal end 43 of the catheter by the pusher shaft 44, the leads 31 and 32 of the string 30 are pulled proximally while the pusher shaft is advanced distally bringing the pusher face 52 flush with the distal end 43 of the catheter. As the string is pulled, the proximal end of the stent 68 butts against the pusher face 52 and distal end 43 of the catheter. The resulting compressive force causes the length of the stent to shorten and its diameter to expand, as the wraps of the stent twist and slide relative to each other. The stent material offers sufficient column strength to resist collapsing under the resulting longitudinal compressive force placed on the stent. The helical orientation of the wraps 13 creates an angled, rather than a square, profile at the proximal end 68 of the stent for contacting the pusher face. However, the stent does not rotate significantly about the angular proximal end 68 during application of compressive force, avoiding potential misalignment of the stent within the vessel. If the stent begins to rotate out of alignment as the string leads are pulled, contact with the walls of the vessel keeps the stent sufficiently aligned so that it then can be expanded fully to support the vessel. After the stent is expanded to become engaged with the vessel, one lead 31 or 32 is pulled proximally to draw the string 30 out of the stent and patient.

Figure 6:
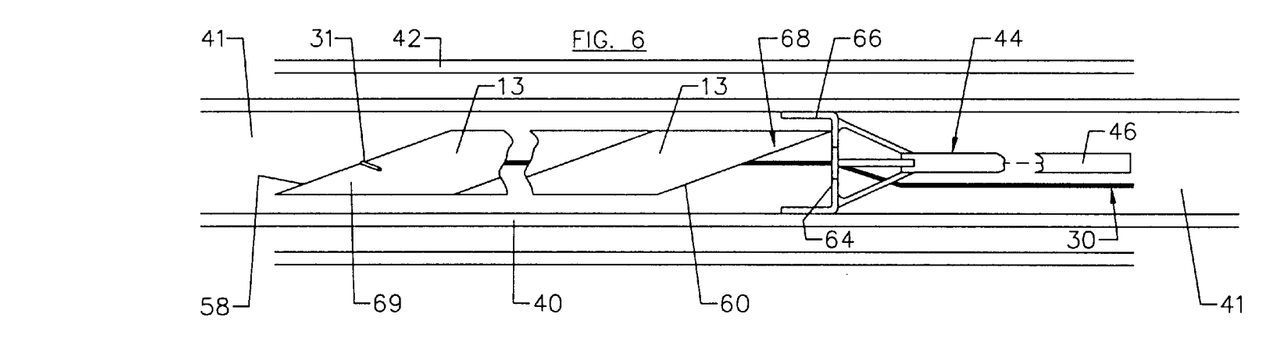
FIG. 6 is a diagrammatic cut away view of the stent being delivered through a guide catheter in a vessel by a delivery system embodiment.
Figure 6A:
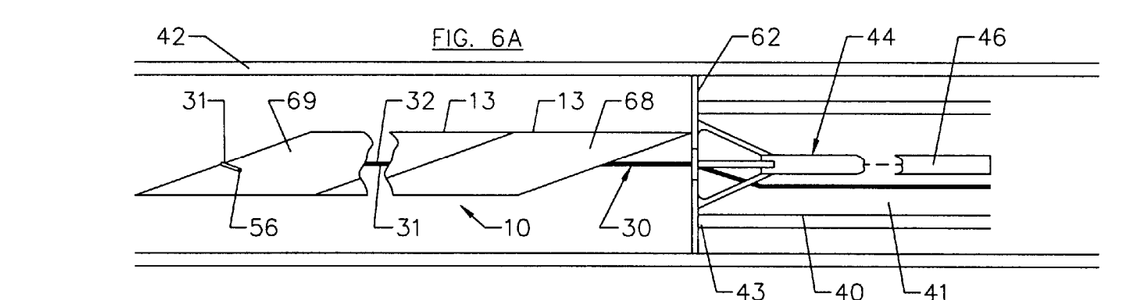
FIG. 6A is a diagrammatic cut away view of the stent being delivered into a vessel by a delivery system embodiment.
Figure 6B:
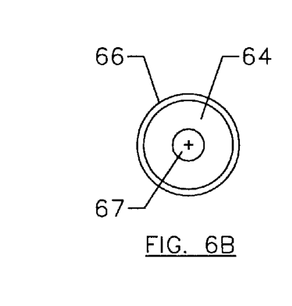
FIG. 6B is a diagrammatic front view of a second pusher shaft embodiment in a collapsed configuration.
Figure 6C:
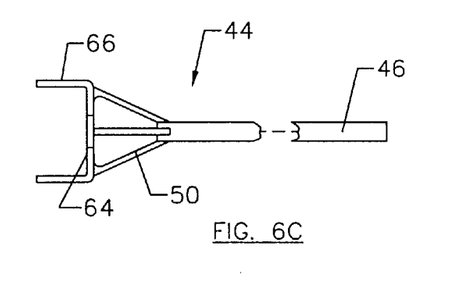
FIG. 6C is a diagrammatic side view of a second pusher shaft embodiment in a collapsed configuration.
Figures 6D, 6E:
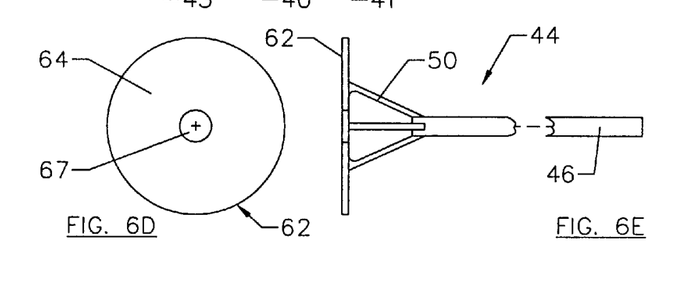
FIG. 6D is a diagrammatic front view of a second pusher shaft embodiment in an open configuration.
FIG. 6E is a diagrammatic side view of a second pusher shaft embodiment in an open configuration.

In an alternative embodiment shown in FIGS. 6–6E the push shaft 44 may comprise a collapsible pusher 62 at its distal end for locating the stent during delivery. The pusher 62 comprises a thin disk of superelastic material, such as nitinol, having an undeformed diameter that is greater than the outside diameter of the guide catheter 40 to provide a broad surface at the distal end 43 of the catheter for the stent to contact during expansion. In a procedure using a 6F guide catheter, the undeformed diameter of the pusher may be on the order of 3.1 mm. The large diameter provides a broad contact face 64 that covers not only the guide catheter lumen 41, but also a small area radially extending from the distal end 43 of the catheter, approaching the wall of the vessel 42 as best seen in FIG. 6A. The broad surface presented by the face 64 prevents the proximal end 68 of the stent 10 from becoming wedged between the guide catheter 40 and vessel 42 as the stent is pulled proximally against the face 64 during expansion.

The superelastic property of nitinol permits the oversized pusher 62 to collapse easily when placed in the lumen 41 of the guide catheter 40 as shown in FIG. 6. In the collapsed condition, the edge of the pusher folds over distally creating a circumferential shield 66 projecting from the face 64 of the pusher. After the stent, collapsed to its reduced diameter delivery configuration, is inserted into the lumen 41 at the proximal end of the guide catheter 40, the pusher 62 of the push rod 44 is collapsed and inserted into the lumen 41 behind the stent. As the pusher 62 is loaded into the guide catheter 40, the stent pull string 30 is threaded through the pusher through hole 67 so that it may be maintained outside the patient as the stent is pushed distally to the deployment site.

As best shown in FIG. 6, the circumferential shield 66 surrounds the proximal end of the stent as it butts up against the pusher face 64 during delivery through the guide catheter 40. Therefore, the circumferential shield 66 helps guide the stent through the lumen, preventing potential misalignment and snagging between the lumen wall and the pusher. As the stent and pusher 62 emerge from the distal end 43 of the delivery guide catheter 40, the edge of the pusher that forms the circumferential shield 66 springs back in plane with the pusher face 64, increasing its surface area. As best shown in FIG. 6A, the face 64 of the expanded pusher covers the lumen 41 of the guide catheter 40 plus a substantial area between the guide catheter 40 and the vessel 42. As the expanded pusher 62 rests against the distal end 43 of the guide catheter, the stent pull string 30 is pulled proximally to cause the proximal end of the stent 60 to butt against the face 64 of the pusher compressing the stent length and radially expanding the stent to contact the vessel 42.

Figure 7:
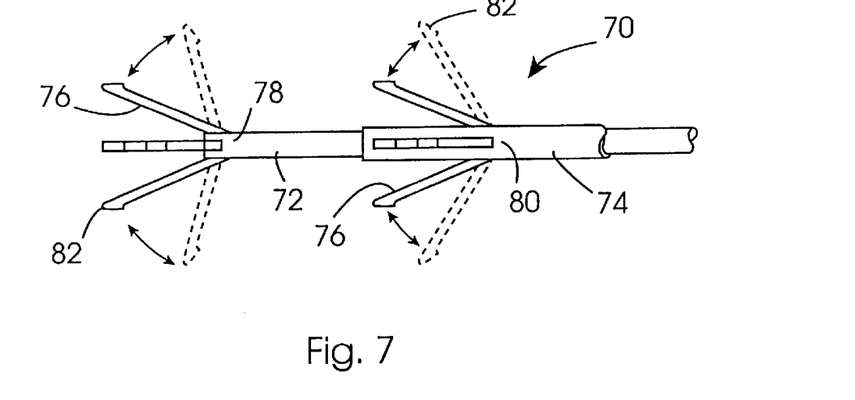
FIG. 7 is a diagrammatic side view of a coaxial delivery shaft showing a contracted position of the struts in solid lines and the extended position of the struts in phantom.

The stent may also be delivered through the guide catheter using a coaxial shaft 70 shown diagrammatically in FIG. 7. The coaxial shaft 70 is comprised of an inner shaft 72 and outer shaft 74 each having several hinged struts 76 spaced radially around respective shaft distal ends 78 and 80. Ends 82 of the struts 76 releasably connect to the interior surface of the stent at holes 84, or alternatively at openings 28. Struts of the inner shaft 72 are joined to a wrap 13 near the distal end 69 of the stent 10 (shown in phantom in FIG. 7A) and the struts 76 of the outer shaft 74 are joined to a wrap 13 at the proximal end 68 of the stent so that when the inner and outer shafts are rotated relative to each other, the wraps 13 of the stent are slid in opposite directions to expand the stent as is shown in FIG. 7B.

As described above, the stent 10 is delivered at the end of the coaxial shaft 70 through a guide catheter that has been navigated to the deployment site within the vessel. Before insertion through the guide catheter, the stent, in a reduced diameter elongated length configuration, is engaged with the ends 82 of struts 76. The inner 72 and outer 74 shafts may be fabricated from any flexible material capable of transmitting a torsional force input at the proximal ends of the shafts to the distal ends of the shafts to twist and slide the wraps 13 of the stent relative to each other. Various plastic materials and stainless steel are known in the art as suitable for producing torsionally rigid shafts sized to fit through the vasculature. The shafts 72 and 74 should be sized to fit easily within the lumen 41 of the guide catheter and within the stent while in its collapsed configuration.

The struts 76 are fabricated from a rigid material, preferably a polymer that is capable of being hingedly mounted to the shafts 72 and 74 to move with the radially expanding stent. The ends 82 of the struts flare outward slightly and terminate in an angled cut, so that only the end of the strut is square with the stent surface to fit into the location holes 84. The remaining portion of the strut is prevented from entering the hole 84 due to the angle formed between the strut and stent surface, while the strut is holding the stent. While the stent is in the collapsed configuration, the end of the strut is flush with the surface of the stent 10 when engaging the location holes 84.

Figure 7A:
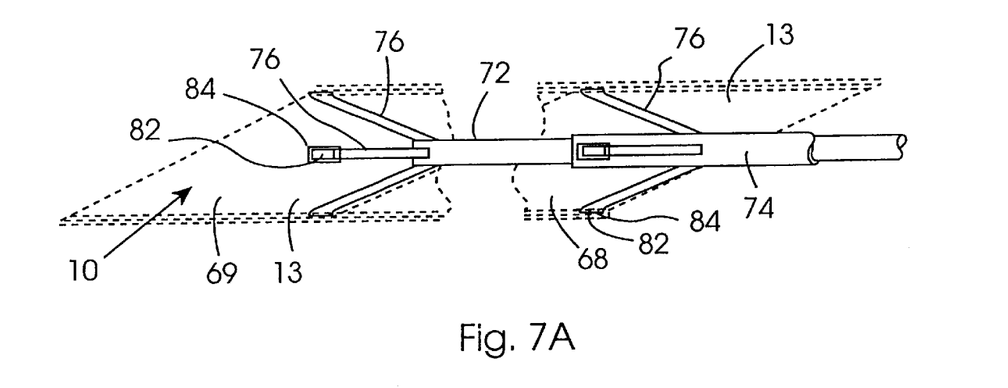
FIG. 7A is a diagrammatic side view of a coaxial delivery shaft with a stent (shown in phantom) in its reduced diameter configuration mounted on the struts.
Figure 7B:
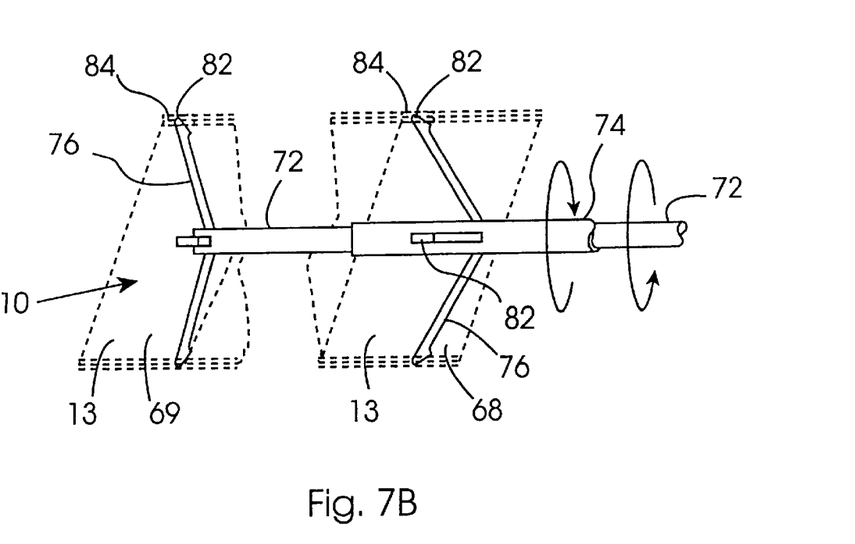
FIG. 7B is a diagrammatic side view of a coaxial delivery shaft with the inner and outer shafts being rotated relative to each other to expand the stent (shown in phantom).

As shown in FIG. 7B, as the stent becomes fully expanded, the end 82 of the strut 76 rotates out of the locating hole 84 while the struts extend with the expanding stent 10 becoming closer to perpendicular to the coaxial shaft. The new orientation of the strut end 82 with the surface of the expanded stent 10 is favorable for permitting the strut ends to be removed from the locating holes 84 as the coaxial shaft 70 is withdrawn proximally out of the stent and back into the guide catheter. The struts 76 are freely hinged to the distal ends 78 and 80 of shafts 72 and 74, moving from their collapsed to extended configurations only by the force of the expanding stent. As the stent expands, the inner shaft 72 may slide within shaft 74 to compensate for the reducing length of the stent. Manipulation of the inner and outer shafts 72 and 74 from outside the patient may be facilitated by a variety of methods known in the art such as attaching separate knobs about the shafts at their proximal ends.

The coaxial delivery mechanism shown in FIGS. 7–7B also provides the advantage of recompressing the stent after it has been expanded and before it has been released from the struts 76 so that it may be repositioned within the vessel. To recompress the stent, the inner and outer shaft 72 and 74 of the coaxial shaft 70 are rotated in relative directions opposite to the directions in which they were rotated to expand the stent. The wraps 13 twist and slide relative to each other to compress and elongate the stent. Such recompression of the stent may be useful if the physician has determined that the stent has not been deployed in the proper vessel location. Reducing the diameter of the stent permits repositioning in the vessel to the correct location, where the stent can be expanded again by rotating the coaxial shafts.

A stent deployed using either the coaxial shaft or the pusher shaft may be subjected to further expansion force by inflating the balloon of a balloon catheter inside the already expanded stent. After the stent has been deployed and the coaxial shaft or pusher shaft is withdrawn from the guide catheter, a balloon catheter may be inserted through a guide catheter and into the expanded stent. Inflating the balloon exerts radially outward pressure against the interior of the stent urging the wraps 13 to slide relative to each other and the stent to expand. Further expansion of the stent may be possible by this procedure by slightly expanding the area of the vessel wall in contact with the stent. However, it is emphasized that follow-up expansion by a balloon catheter is optional and that the methods and devices described above are intended to provide adequate deployment of the stent within the vessel.

Alternatively, the stent may be delivered and expanded by a balloon catheter. By this method, the stent is placed over the deflated balloon of the catheter and the wraps of the stent slid relative to each other to reduce the diameter of the stent to create close contact with the balloon. The catheter and stent combination are navigated to the intended location within the vessel through a guide catheter previously positioned within the vessel. At the vessel deployment site the balloon is inflated to expand the stent radially. The expansion force of the balloon causes the wraps 13 of the stent to slide relative to each other to cause the stent to expand to engage the vessel. After the stent is expanded, the balloon is deflated and the catheter withdrawn proximally from the stent.

It should be understood that the foregoing description of the invention is intended merely to be illustrative thereof and that other embodiments, modifications and equivalents may be apparent to those skilled in the art without departing from its spirit and principles.

Having thus described the invention, what we desire to claim and secure by Letters Patent is:

1. A stent comprising:
   a strip of biocompatible material having a surface and opposing edges;
   a groove formed along one edge of the strip; and
   a tongue formed along the opposing edge of the strip for interlocking and slidable engagement with the groove such that the strip is helically wrapped and is maintained in a tubular configuration with the engaged tongue and groove extending helically around the tube.

2. The stent of claim 1 further comprising helical wraps of strip material defined by the engaged tongue and groove extending helically around the tube, the wraps being slidable relative to each other to cause the diameter and length of the tube to vary interdependently.

3. The stent of claim 2 wherein the wraps are arranged to translate a compressive force applied at longitudinal ends of the tube into a radial expansion of the tube and translate a tensile force applied at longitudinal ends of the tube into radial compression of the tube.

4. The stent of claim 1 wherein the surface of the strip has a plurality of openings.

5. The stent of claim 1 wherein the strip is formed from a polymer.

6. The stent of claim 1 wherein the strip is bioabsorbable.

7. The stent of claim 1 wherein the strip having a tongue and groove comprises a molded material.

8. The stent of claim 1 wherein the strip having a tongue and groove comprises an extruded material.

9. The stent of claim 1 further comprising:
   a ratcheting mechanism cooperatively formed on the tongue and groove to control the slidable engagement of the tongue within the groove.

10. A method of forming a stent comprising:
    forming a flexible strip of material having a groove along one edge and a tongue along an opposing edge, the tongue being interlockingly and slidably receivable in the groove,
    bringing opposite corners of the strip together and introducing the tongue into the groove,
    advancing the tongue edge along the groove edge to cause the strip to become a helically wrapped tube.

11. A method of deploying a stent in a body lumen comprising:
    providing a stent formed from a strip having an engagable tongue and groove along opposing edges of the strip that has been helically wrapped, with tongue and groove engaged, to form a tube of multiple wraps,
    providing a guide catheter having proximal and distal ends and at least one lumen capable of receiving the stent,
    navigating the delivery catheter to the deployment site within the body lumen,
    pushing the stent through and out the distal end of the guide catheter that has been navigated to a deployment site within the body lumen,
    sliding the wraps of the stent relative to each other to expand the stent into contact with the body lumen.

12. A method of deploying a stent in a body lumen comprising:
    providing a stent formed from a strip having an engagable tongue and groove along opposing edges that has been helically wrapped, with tongue and groove engaged, to form a tube of multiple wraps,
    providing a guide catheter having proximal and distal ends and at least one lumen capable of receiving the stent,
    providing a drawstring attached to the distal end of the stent and being longer than the guide catheter,
    providing a pushing shaft having proximal and distal ends that is slidable within the guide catheter,
    navigating the guide catheter to the deployment site within the body lumen,
    sliding the wraps of the strip relative to each other to reduce the diameter of the tube to a delivery diameter and inserting the stent into the distal end of the catheter,
    pushing the stent out of the distal end of the guide catheter with the pushing shaft,
    pulling the draw string proximally to cause the stent to butt against the distal end of the catheter and/or the pushing shaft to compress the length of the stent and radially expand the stent into contact with the body lumen.

13. A method of deploying a stent in a body lumen comprising:
    providing a stent formed from a strip having an engagable tongue and groove along opposing edges that has been helically wrapped, with tongue and groove engaged, to form a tube of multiple wraps,
    providing a guide catheter having proximal and distal ends and at least one lumen capable of receiving the stent,
    providing a coaxial shaft, slidable within the guide catheter and having inner and outer shafts that are slidable and rotatable relative to each other and that each have struts that are engageable with the stent,
    navigating the guide catheter to a deployment site within the body lumen,
    sliding the wraps of the strip relative to each other to reduce the diameter of the tube to a delivery diameter and inserting the stent onto the strut,
    pushing the stent through and out of the distal end of the guide catheter at the deployment site while joined to the coaxial shaft,
    rotating the inner and outer shafts relative to each other to slide the wraps of the stent in opposite directions to radially expand the stent into contact with the body lumen.

14. A method of repositioning a stent within a body lumen comprising:

provided a stent formed from a strip having an engagable tongue and groove along opposing edges that has been helically wrapped, with tongue and groove engaged, to form a tube of multiple wraps, sliding the wraps relative to each other to reduce the diameter and elongate the stent, moving the reduced diameter stent to a new site within the body lumen;

sliding the wraps relative to each other to expand the stent into contact with the body lumen.

15. A method of repositioning a stent within a body lumen comprising:

providing a stent formed from a strip having an engagable tongue and groove along opposing edges that has been helically wrapped, with tongue and groove engaged, to form a tube of multiple wraps, providing a guide catheter having proximal and distal ends and at least one lumen capable of receiving the stent, providing a coaxial shaft, slidable within the guide catheter and having inner and outer shafts that are slidable and rotatable relative to each other and that each have struts that are engageable with the stent, navigating the guide catheter to a deployment site within the body lumen, sliding the wraps of the strip relative to each other to reduce the diameter of the tube to a delivery diameter and inserting the stent onto the strut, pushing the stent through and out of the distal end of the guide catheter at the deployment site while joined to the coaxial shaft, rotating the inner and outer shafts relative to each other to slide the wraps of the stent in opposite directions to radially expand the stent into contact with the body lumen, subsequently rotating the inner and outer shafts relative to each other to slide the wraps relative to each other to cause the stent to contract away from the body lumen, repositioning the stent within the body lumen;

rotating the inner and outer shafts relative to each other to slide the wraps of the stent in opposite directions to radially expand the stent into contact with the body lumen.

16. A method of deploying a stent in a body lumen comprising:

providing a stent formed from a strip having an engagable tongue and groove along opposing edges that has been helically wrapped, with tongue and groove engaged, to form a tube of multiple wraps, providing a guide catheter having proximal and distal ends and at least one lumen capable of receiving the stent, providing an expandable member located within the stent, navigating the delivery catheter to the deployment site within the body lumen, guiding the stent and expandable member through and out the distal end of the guide catheter that has been navigated to a deployment site within the body lumen, expanding the expandable member within the stent to cause the wraps of the stent to slide relative to each other to expand the stent into contact with the body lumen.

17. A method of deploying a stent in a body lumen comprising:

providing a stent formed from a strip having an engagable tongue and groove along opposing edges that has been helically wrapped, with tongue and groove engaged, to form a tube of multiple wraps, providing a guide catheter having a proximal and distal ends and at least one lumen capable of receiving the stent, providing a balloon catheter sized to be placed within the stent, navigating the guide catheter to the deployment site within the body lumen, placing the balloon within the stent and sliding the wraps of the strip relative to each other to reduce the diameter of the stent so that it contacts the balloon, inserting the stent and balloon catheter into the proximal end of the guide catheter, guiding the stent and balloon through and out the distal end of the guide catheter, inflating the balloon within the stent to cause the wraps of the stent to slide relative to each other to radially expand the stent into contact with the body lumen.

18. A stent and delivery system comprising:

a stent formed from a helically wrapped strip of biocompatible material with opposing edges of the strip slidably interlocked with each other;

a catheter having at least one lumen sized to slidably receive the stent;

a pusher having an elongate shaft sized to be slidable in the catheter lumen and longitudinally push a proximal end of the stent; and a pulling member coupled to said stent.

19. A stent and deliver system comprising:

a stent formed from a helically wrapped strip of biocompatible material with opposing edges slidably interlocked with each other;

a catheter having at least one lumen sized to slidably receive the stent;

elongate coaxial shafts sized to be slidable in the catheter lumen, each shaft having a distal end that is releasably connected to the stent.

* * * * *